United States Patent [19]

Suh et al.

[11] Patent Number: 4,932,243

[45] Date of Patent: Jun. 12, 1990

[54] MOISTURE MEASUREMENT DEVICE

[75] Inventors: Nam P. Suh, Sudbury; Francis A. Waldman, Somerville; Richard E. von Turkovich; Douglas M. Chin, both of Cambridge; Thomas H. Lee, Somerville, all of Mass.

[73] Assignee: Axiomatics Corporation, Cambridge, Mass.

[21] Appl. No.: 402,963

[22] Filed: Sep. 5, 1989

Related U.S. Application Data

[63] Continuation of Ser. No. 936,889, Dec. 2, 1986, abandoned, which is a continuation-in-part of Ser. No. 754,333, Jul. 12, 1985, abandoned.

[51] Int. Cl.$^5$ ............................................. G01N 27/22
[52] U.S. Cl. ...................................... 73/73; 324/664; 364/556; 374/115
[58] Field of Search ................ 73/73; 324/61 R, 61 P; 361/282, 286; 364/556, 557, 568; 374/115, 142

[56] References Cited

U.S. PATENT DOCUMENTS

| | | | |
|---|---|---|---|
| 3,623,367 | 11/1971 | Benedict | 374/115 |
| 3,778,707 | 12/1973 | Vogel | 324/61 P |
| 3,979,581 | 9/1976 | Reuland | 324/61 R |
| 4,133,208 | 1/1979 | Parlanti | 374/178 |
| 4,174,498 | 11/1979 | Preischat | 324/61 R |

FOREIGN PATENT DOCUMENTS

| | | | |
|---|---|---|---|
| 662387 | 4/1963 | Canada | 73/73 |
| 1080801 | 4/1960 | Fed. Rep. of Germany | 73/73 |
| 2537977 | 3/1976 | Fed. Rep. of Germany | 324/61 R |
| 491886 | 3/1976 | U.S.S.R. | 324/61 R |
| 1030715 | 7/1983 | U.S.S.R. | 324/61 R |

OTHER PUBLICATIONS

Tomokazu Arai et al., "Small Moisture Content Measurement, . . . Dielectric Loss Method", IEEE Transactions of Instrumentation and Measurement, vol. IM-26, No. 2, Jun. 1977, pp. 148–152.

Primary Examiner—William A. Cuchlinski, Jr.
Assistant Examiner—W. Morris Worth
Attorney, Agent, or Firm—Robert F. O'Connell

[57] ABSTRACT

A method of determining the moisture content of a material in which the material is caused to flow continually through a sensor region, the spatially averaged temperature of the material being continually determined independently of the dynamic thermal response of the material. The loss and capacitance of the sensor is also continually determined, the moisture content of the material than being determined in response to the spatially averaged temperature and the loss and capacitance determinations independently of changes in the packing density of the material as it continually flows through the sensor region.

17 Claims, 2 Drawing Sheets

MOISTURE MEASUREMENT DEVICE

This is a continuation of Ser. No. 06/936889 filed Dec. 2, 1986 now abandoned which is a continuation-in-part of Ser. No. 06/754,333 filed on July 12, 1985 now abandoned.

INTRODUCTION

This invention relates generally to techniques for continually determining the moisture content of a continually flowing material, and more particularly, to improved techniques for doing so, independently of static or dynamic variations in temperature and packing density of the flowing material.

BACKGROUND OF THE INVENTION

Many techniques have been devised for monitoring the moisture content of a material, but most of these techniques utilize discrete samples, or batches, of material and are not applicable to a continuously flowing, or on-line, production environment. For example, known techniques for use in batch processing of materials have been described in various patents, including U.S. Pat. Nos. 3,781,673 issued on Dec. 25, 1973 to Resh, 4,050,016 issued Sept. 20, 1977 to Marsh et al., 4,147,976 issued on Apr. 3, 1979 to Wang, 4,174,498 issued on Nov. 13, 1979 to Preikschat, 4,352,059 issued on Sept. 28, 1982 to Suh et al., 4,399,404 issued on Aug. 16, 1983 to Resh, 3,979,581 issued on Sept. 7, 1976 to Reuland, and 3,778,707 issued on Dec. 11, 1973 to Vogel. None of the techniques described therein is applicable to on-line production applications wherein the material whose moisture content is to be measured is continually flowing.

In polymer processing, for example, it is generally desirable to determine moisture content with a resolution of the order of 100 parts per million (ppm). Such precise determination of moisture content in flowing materials is a particularly difficult problem in view of the multitude of factors that can corrupt the measurement. The two most important influences are those of material temperature and material packing density variation.

In those systems described in certain of the above patents which discuss the problem of changes in the packing density of the sample being measured, the proposed solutions to this problem are generally not applicable to continually-flowing, on-line systems. For example, certain patents propose solving this problem either by measuring the weight of discrete samples removed from the batch of material or by making a sample container that is configured and operated to encourage a particular packing density for each sample. Such approaches are clearly not feasible or economical for on-line moisture monitoring systems.

In addition, only the Suh et al., Preikschat, Reuland, and Vogel patents disclose the use of measurements of dielectric loss of the samples involved for monitoring moisture content. In Preikschat, for example, measurements of both dielectric loss and capacitance are made, but neither quantity is used in a way to compensate for packing density variations. It is believed that the basic reason that none of the aforesaid known systems is able to provide a satisfactory technique for compensating for packing density changes in an on-line system is that measuring the small amounts of dielectric loss present in most materials is considerably more complicated than merely measuring the dielectric constant of the material. While in systems dealing with most non-plastic materials whose moisture contents are much higher than those of plastic materials, simply measuring the effect of moisture on the dielectric constant may be sufficient. However, in systems dealing with plastic materials, measurement of the dielectric constant alone is clearly inadequate. Moreover, the computational complexity involved in implementing a suitable technique for compensating for packing density makes it difficult to achieve such compensation in a purely analog system as such previous systems are typically configured.

While the method disclosed by Reuland incorporates dielectric loss data to compute moisture content independently of packing density variations in an on-line situation, the approximations that necessarily attend the use of polynomials of relatively low order may result in large errors when significant packing density variations occur. In principle, higher-order polynomials could be employed to extend the range over which the compensation for density variation is effective. Unfortunately, the number of calibration experiments that must be performed increases, since "n" independent experimental points are required to specify uniquely an nth-order polynomial. This empirical burden can become quite severe (i.e., "n" must be rather large) when seeking measurement resolutions on the order of 100 ppm as desired, limiting the practicality of such an approach.

Although it may not always be practical to compute moisture content accurately at all times, it is often possible to identify when errors are likely to be unacceptably large, and to provide some indication to the user as to this fact. For example, if the sensor is not filled with a sufficient quantity of material, its capacitance will be less than if the packing density were higher. Below a certain critical packing density, the relationship between loss and capacitance (viz., FIG. 3) may no longer be substantially linear, as assumed. Accordingly, it is desirable to indicate when the packing density is insufficient for accurate determination of moisture contents. As can be seen from examination of FIG. 3, a low packing density can be readily detected as insufficient capacitance, e.g., the operating regime to the left of dashed line 29. The precise location of dashed line 29 is best determined by experiment. Once determined, the moisture algorithm (described later) can be modified to signal the condition of insufficient packing density based on the measurement of capacitance.

Another critical factor in monitoring moisture contents of flowing materials concerns the temperature of the flowing material. The critical nature of the temperature measurement problem in this context is not generally appreciated by those in the art, and little attention has been paid to this problem in prior art systems. Although Reuland discusses an extension of his method that incorporates temperature information, several factors mitigate against doing so in a straightforward manner. First, a spatial temperature average is needed to account for spatial thermal gradients that inevitably arise in a flowing material. Such averaging is necessary because a temperature measurement error of as little as one degree Celsius can result in a moisture measurement error of as much as 1000 ppm in some materials.

Another critical temperature-related consideration is that of matching the dynamic behavior of the temperature measurement apparatus to the actual dynamic thermal behavior of the material under test. This matching is necessary to insure that the temperature indicated by the thermometric apparatus does in fact reflect the actual temperature of the material under test at all times, even when the material is actively heated or cooled during processing. For example, most temperature apparatus tends to respond to the temperature of both the flowing material and the air, a situation that is generally unavoidable because such apparatus is in physical contact with both the air and the flowing material. However, the volume-averaged temperature of the flowing material tends to lag behind that of the air under dynamic conditions. Hence, the temperatures as reported by the thermometric apparatus tend to lead those of the actual flowing material, introducing errors. Thus, some compensation for this mismatch in thermal dynamic behavior must be provided if accurate determination of moisture contents is to be made under dynamically varying temperature conditions.

Yet another problem related to temperature concerns a dielectric property of materials. In certain polymers, for example, there exists a region of temperature in which the dielectric properties exhibit substantially no sensitivity to moisture content, although the material may exhibit significant sensitivity to moisture at tempratures above and below this critical region. Furthermore, typically below a certain temperature, the dielectric properties of most materials exhibit substantially no sensitivity to moisture content.

U.S. patent application Ser. No. 489,319, filed on Apr. 28, 1983 by Suh et al., has proposed an on-line moisture measurement system that incorporates a measurement of dielectric loss and that provides in the overall system techniques for compensating for variations in dielectric loss in a sensor full of material due to variations in temperature and to variations in packing density of the material as it flows through a sensor element. Such a technique requires a relatively complicated sensor device which utilizes a pair of reference cells having known moisture contents, one having a substantially zero moisture content and the other having a moisture content substantially equal to the maximum moisture content expected in the material which is being processed. The difference between the dielectric losses of the materials in the first and second reference cells is used to compensate automatically for variations in loss of the sensor due to variations in temperature. Further, the system provides a signal output proportional to packing density to compensate for changes in this parameter. The signal output is combined with the measured signal which represents the dielectric loss difference between the flowing material and the material in one of the reference cells to compensate for changes in packing density.

While the latter system is the first one known to provide for automatic temperature and packing density compensation in an on-line system, certain disadvantages occur in making and using such systems. For example, it is found that the moisture content measurement is subject to errors which arise due to the technique itself as well as to changes in the characteristics of the reference cells which are used. Moreover, when a different material is utilized, a different pair of reference cells is required and the reference cells have to be replaced continually for on-line measurements of different materials. Further, even when using the same material the characteristics of the reference cells tend to change with age and for that reason also they must be periodically replaced. Additionally, the overall system tends to be physically cumbersome to install and use and relatively expensive to make and maintain.

In view of the foregoing considerations, it is evidently necessary to combine sensitive dielectric capacitance and loss measurements with sophisticated temperature measurement to compute accurately the moisture content of continually flowing materials. Further, such measurements should use techniques which are relatively easy to install and use, which do not cause large errors during use or with age, and which can be made and maintained at reasonable cost. In addition, to assure that inaccurate readings do not result from density variations or material temperatures that lie outside of some anticipated range, some indication of such a departure from normal operating regimes must also be provided.

BRIEF SUMMARY OF THE INVENTION

The aim of the present invention is to provide improved accuracy of moisture content determinations of flowing materials, independently of both spatial and temporal variations in temperature and in packing density, utilizing a system which can be made at reasonable cost and used in a relatively easy manner.

In accordance with these aims, a system for performing on-line moisture content measurements utilizes a microprocessor which implements an algorithm for performing the desired measurement operation. A sensing element used therein is arranged to permit a continually flowing material to flow through a region defined by the sensor structure. As the material flows therethrough, a spatially averaged temperature of the flowing materials is determined by using suitable measurement techniques. In addition, the dynamic thermal behavior of the sensor is matched to the dynamic thermal behavior of the flowing material so that the sensed temperature substantially reflects the actual temperature of the material at all times. Further, the dielectric loss and capacitance of the sensor element are simultaneously measured as the material flows through the sensor.

The microprocessor responds to the values of such spatially averaged and dynamically matched temperature values, and to such dielectric loss and capacitance values which are so determined and continually determines the moisture content of the flowing material as a function thereof by utilizing a carefully devised program for such determination. Such a program is derived using a technique for closely approximating the dielectric loss vs. capacitance relationship for different temperatures and different packing densities at known moisture contents.

It is found that by utilizing such an approach, a program can be devised so that the moisture content can be continually determined as a function of temperature, dielectric loss and capacitance in an accurate and readily implemented manner at a reasonable cost, independently of changes in the packing density of the continually flowing material. Such a technique is useful for measuring the moisture content of any material without the need to provide any changes in the sensing element. In addition, the approach can be readily adapted to utilize various sizes of sensor elements, which varying sizes tend to cause changes in the measured loss and capacitance.

DESCRIPTION OF THE INVENTION

The invention is described in more detail with the help of the accompanying drawings wherein.

Figure 1:
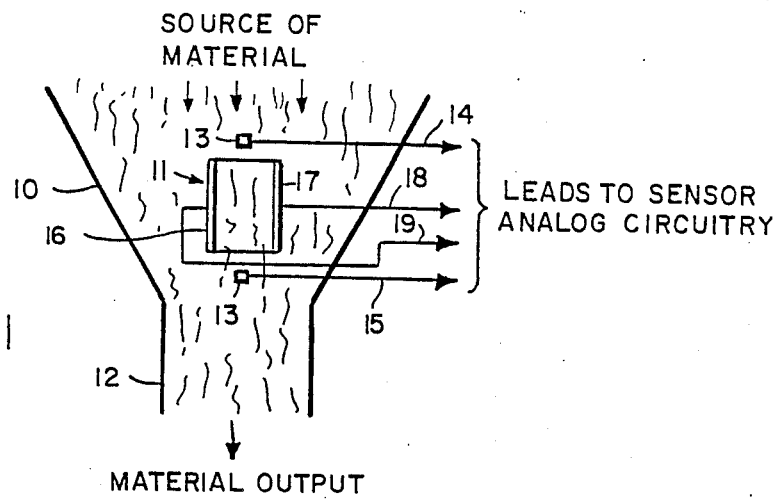
FIG. 1 shows a diagrammatic view of a portion of an overall moisture monitoring system in which material continually flows through a sensing region thereof.

As can be seen diagrammatically in FIG. 1 a source of a material whose moisture content is to be determined can be used to supply such material to a hopper 10 in which is placed a sensing element 11. The material, for example, may be plastic material in the form of small pellets, such pellets continually flowing through and around the sensing element region 11 due to gravity, for example, as shown. The pellets are then supplied to the reduced diameter output end 12 of the hopper for use in whatever application the material is to be utilized. It is desired that the moisture content of the material be monitored as it continually flows through the hopper.

As part of the overall sensing element at least a pair of temperature sensors 13 is suitably positioned relative to the flowing material, e.g., with at least one placed just above and at least one placed just below the electrodes of sensing element 11, and temperature sensor output voltages representing the temperatures of the flowing material are supplied on leads 14 and 15 for use in calculating the moisture content of the material as discussed in more detail below.

In its simplest form the sensing element includes a pair of electrode plates 16 and 17 defining a region through which material continually flows, the voltage across such plates being supplied on leads 18 and 19 so as to be utilized in measuring the capacitance and dielectric loss between the plates as the material is continually flowing therethrough.

Figure 2:
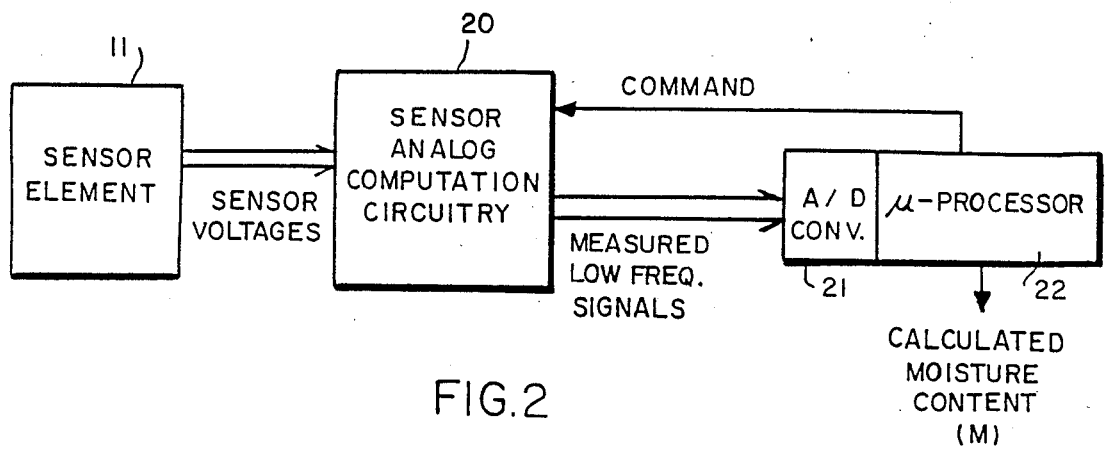
FIG. 2 shows a block diagram depicting the signals handled by a moisture monitoring system in accordance with the invention.

FIG. 2 depicts in block diagram form an overall voltage handling system. As seen therein, sensor element 11 supplies the output sensor voltages discussed above substantially simultaneously to sensor analog computation circuitry. The circuitry utilized therein provides DC output signals representing the sensed temperature, the current into the sensor, and the voltage across plates 16 and 17, which voltages are utilized to calculate the dielectric loss and the capacitance between the electrodes 16 and 17, as well as the average temperature of the flowing material as sensed by the temperature sensor 13. Such signals can be supplied upon command by an appropriate signal for actuating such circuits when received from a microprocessor 22. The DC signals can be converted into digital signals utilizing an A/D (analog-to-digital) conversion element 21, as would be well known to the art. The digital signals can then be operated upon by a microprocessor for determining the average temperature (T), the dielectric loss (Lm), and the capacitance (C), using well-known techniques, which parameters can then be utilized by the microprocessor as discussed below for determining the moisture content of the material as it is continually flowing through the region of the sensing element 11.

Figure 3:
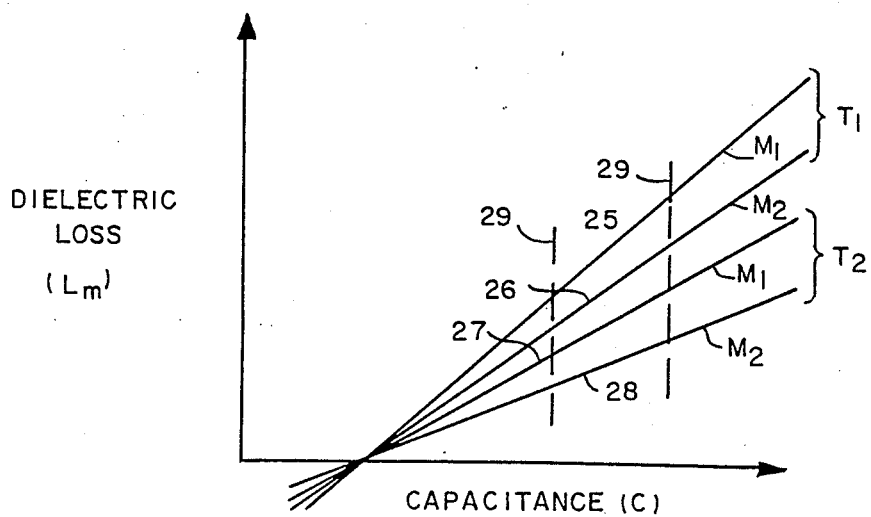
FIG. 3 shows a graph of curves of loss vs. capacitance for various samples of a material, which curves are useful in deriving an algorithm used in accordance with the invention.

In order to understand how the algorithm for determining moisture content, as utilized by the microprocessor, is derived, it is helpful to consider the graph of FIG. 3. If samples of a material whose moisture content is to be determined are obtained, and if each sample is arranged to have a known packing density, it is possible to plot changes in dielectric loss as a function of the capacitance of such material at specified temperatures and moisture contents. Thus, if four such samples are utilized, dielectric loss vs. capacitance curves can be plotted for samples which all have the same packing density at two different known temperatures T1 and T2 and for two different known moisture contents M1 and M2. Over a particular range of densities which are expected in the continuously flowing material, such curves of dielectric loss vs. capacitance can be relatively accurately approximated as straight lines. Four samples having known moisture contents M1 or M2 at known temperatures T1 or T2 are plotted as curves 25, 26, 27, and 28 in the manner shown in FIG. 3.

As can be seen from the graph, such curves tend to intersect at a point having roughly zero dielectric loss, and a capacitance that is higher than the capacitance of the sensor element when it is empty (i.e., when no material is present within the sensor). The temperatures T1 and T2 for making such measurements can be selected so that one is relatively close to the lowest expected operating temperature of the system and the other is relatively close to the highest expected operating temperature of the system.

A linearly approximate equation for dielectric loss (Lm) as a function of capacitance (C) for varying temperatures and varying moisture contents can be devised as follows:

$$Lm = (Ko + Kt*T + Km*M + Ktm*T*M)*C + (Bo + Bt*T + Bm*M + Btm*T*M) \quad (1)$$

Each of the curves 25-28 over the range of capacitances depicted between the dashed lines 29 can be approximated very accurately as a straight line, having a known slope (mathematically related to the B coefficients) and known intercept (mathematically related to the K coefficients). Examination of Eq. (1) shows eight unknown coefficients (Ko, Kt, Km, Ktm, Bo, Bt, Bm, and Btm). Each of such curves in addition has a known temperature and a known moisture content. Accordingly, for such conditions Eq. (1) can be solved using mathematical techniques well known to that art to determine the eight K and B coefficients specified above.

Eq. (1) can be used to provide a reasonable approximation over a particular reasonable range of parameters for many applications, especially since packing tends to be a linear phenomenon even though the thermal response of the material tends to be non-linear. In some applications it may be desirable to use a non-linear approximation by utilizing a higher-order equation for such a purpose. One such equation, for example, may be of the following form:

$$Lm = (A*T + B*T^2 + D*T^3 + E*T^4 + F*M + G*M^2)*C + (H*T + I*T^2 + J*T^3 + K*T^4 + N*M + O*M^2) \quad (1A)$$

Once the coefficients are determined, Eq. (1) can be placed in a different form to solve for the moisture content M as follows:

$$M = \frac{Lm - (Ko + Kt*T)*C - (Bo + Bt*T)}{(Km + Ktm*T)*C + (Bm + Btm*T)} \quad (2)$$

As can be seen in Eq. (2) the moisture content can be computed as a function of dielectric loss Lm, average temperature T, and capacitance C once the K and B coefficients have been determined. Such a computation can be made utilizing a microprocessor which is programmed to solve Eq. (2) using known techniques for preparing an algorithm for such purpose. For example, a microprocessor well known to the art, such as the model 8086 made and sold by Intel Corporation, can be readily prepared by using techniques well known to those in the art to solve Eq. (2). In response to digital input information with respect to the average temperature T, the dielectric loss Lm, and the capacitance C of the material flowing through the sensor element, the moisture content as determined in accordance with Eq. (2) produces an accurate computation thereof that is substantially independent of the packing density so that, in effect, compensation for changes in packing density is automatic.

It is further found that the capacitance values change as a function of the size of the sensor element 11 (in effect the size of the region defined by the sensor element through which the material flows). Accordingly it is necessary to take such changes into account in Eq. (2) when sensor elements having different sizes are utilized.

The manner in which such changes can be compensated for in implementing the aglorithm for solving Eq. (2) is to utilize a particular sensor element of known size as a reference value and to determine the capacitance Cor of such a reference element when said sensor element has no material therein (an empty sensor) and to utilize a correction factor which is represented by the ratio of the capacitance Com for another different size sensor element, also as measured without any material therein, relative to the capacitance of the empty reference size element, i.e., the ratio Com/Cor. Such a factor need be utilized only in conjunction with those terms of Eq. (2) which relate to the intercept of the curves shown in FIG. 3 since capacitance changes as a function of size have little effect on the actual slope of the curve.

Thus, eq. (2) can be revised for different sizes of sensor elements as shown in Eq. (3) as follows:

$$M = \frac{Lm - (Ko + Kt*T)*C - (Bo + Bt*T)*Com/Cor}{(Km + Ktm*T)*C + (Bm + Btm*T)*Com/Cor} \quad (3)$$

As can be seen therein, terms related to the B coefficients are corrected in accordance with the ratio Com/Cor which correction thereby permits Eq. (3) to take into account the moisture content of the material when using a sensor element of a different size from that of the reference sensor element.

The programming of the microprocessor to solve Eq. (3) would also be well within the skill of the art for use with any suitably selected microprocessor as discussed above. Although the characteristics of the samples of material used to generate the curves of FIG. 3 permit the coefficients for such material to be obtained so that the above equations can be solved for such particular material by the microprocessor, the microprocessor can also be used for handling the same general equations for use with other different materials by performing the same process for determining the K and B coefficients involved utilizing four samples of each of the different materials which may be involved. Different sets of K and B coefficients for different materials can be appropriately stored and selected by the microprocessor for implementing the equations for such different materials as required. Accordingly, the system of the invention can be used for many materials, so long as the coefficients required for such materials have been appropriately determined and stored for use by the microprocessor, and for any sensor element size so long as the appropriate ratios of the capacitances (when empty) are suitably determined and also stored for use by the microprocessor.

The use of a microprocessor to implement the solution of the above equations overcomes the disadvantages of the on-line system described in the Suh et al. patent discussed above, for example, in that such use does not depend on the use of reference samples, the characteristics of which change with time, and does not require the changing of reference samples for different materials. Moreover, it is believed that the implementation of a computational system using a microprocessor can be done for lower cost than previously suggested systems. Additionally, the use of the aforesaid straight line approximations and the microprocessor computational capability permit a very accurate determination of moisture content for continually flowing materials.

While the invention has been described utilizing a simple sensor element formed as a pair of electrode plates 16 and 17 together with a pair of temperature sensing elements 13 in FIG. 1, FIGS. 3–6 depict a more sophisticated embodiment of a sensor element which is currently preferred for use in the system of the invention. As can be seen in such figures, the sensor element comprises a pair of concentric cylindrical elements 30 and 31, element 30 representing an outer electrode and element 31 representing an inner electrode. A third concentric element 33 is positioned substantially halfway between elements 30 and 31 which element is also concentric therewith. Element 33 effectively comprises a split cylindrical configuration such that three, separate cylindrical elements 33a, 33b, and 33c are utilized as shown.

Figure 4:
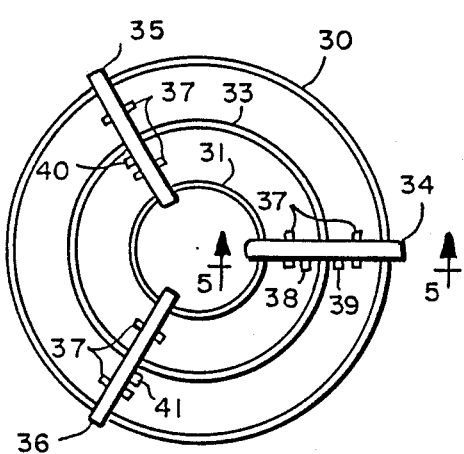
FIG. 4 shows a plan view of a particular embodiment of a sensor element which has been successfully used as the sensor in the embodiment of FIG. 1.
Figure 5:
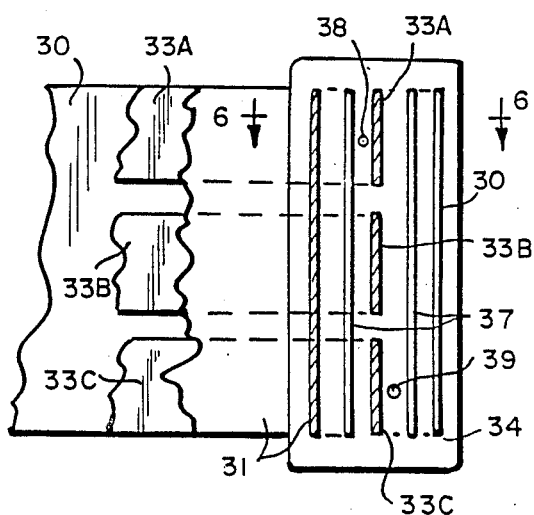
FIG. 5 shows a view in section through lines 5—5 of FIG. 4.
Figure 6:
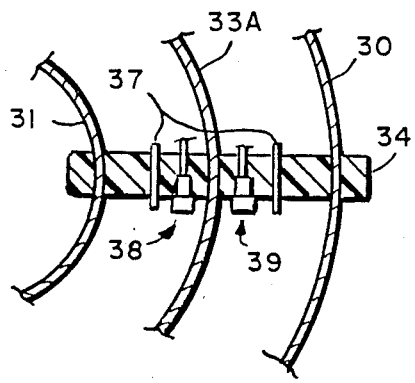
FIG. 6 shows a view in section through lines 6—6 of FIG. 5.

A plurality (in this case, three) of insulating struts 34, 35, and 36 are used to support the cylindrical elements 30, 31, and 33. As can be seen in the section views of a particular strut 34, for example, in FIGS. 5 and 6, the cylindrical elements pass through the strut and each strut includes a pair of shield members 37 between the split cylindrical elements 33 and the inner and outer cylindrical elements 30 and 31, respectively, as shown. The shield elements 37 extend substantially along the length of the strut and project slightly beyond the lateral sides thereof, as seen in FIG. 6. A pair of temperature sensing elements 38 and 39 is placed on one side of strut 34 while additional temperature sensing elements 40 and 41 are placed on the sides of struts 35 and 36, respectively, as best shown in FIG. 4. The shield elements 37 are used to prevent any adverse measurement effects due to the struts themselves as well as to act as barriers for minimizing the effects of surface conductivity on the struts which may be due to dust, etc.

Figure 8:
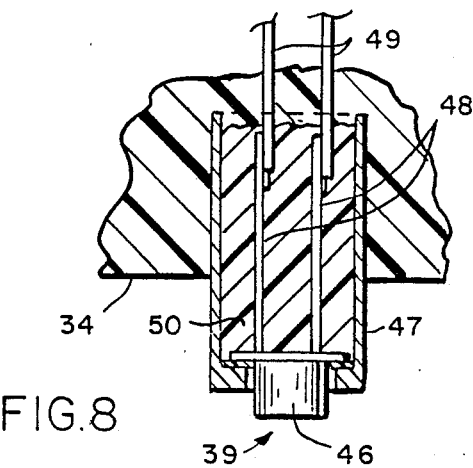
FIG. 8 shows a more detailed view in section of an embodiment of a temperature sensing element.

Since the spatial and temporal variations in temperature in the flowing material must be accurately determined in order to provide an effective measurement system for achieving the desired resolution (e.g., approximately 100 ppm), the temperature sensing elements are configured in accordance with the invention in a specific manner so as to assure that the temperature sensed in each case accurately represents the temperature of the material rather than the temperature of the air surrounding them. Accordingly, a plurality of temperature sensors is used at various positions within the overall sensor elements so as to provide a spatially averaged temperature measurement in response thereto. Further, the temperature sensors are arranged so that the thermal response characteristics of each sensor substantially approximate, or match, the thermal response characteristics of the flowing material. Such thermal response characteristics can be achieved as in a particular embodiment by the configuration shown in FIG. 8. As seen therein, an exemplary temperature sensor structure 39 includes a thermally sensitive diode 46, an example of which is one made and sold by National Semiconductor Corporation under the model designation LM135, the diode being mounted within a stainless steel collar member 47. The collar member extends into an opening in a strut, e.g., strut 34. Electrical leads 48 extend from the diode through the collar member where they are soldered to Teflon-coated wires 49 which can be brought out from the opposite side of the strut to the electronics circuitry. The leads and Teflon wires are encapsulated with a high temperature epoxy material 50 which can be the same as the epoxy material which forms the strut. Such a material may be, for example, that made and sold by Bacon Industries of Newton, Mass. under the designation P-85.

Figure 9:
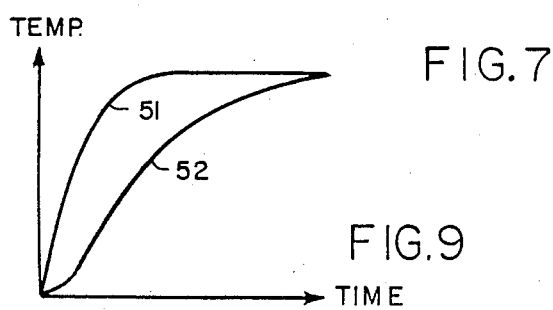
FIG. 9 shows curves of temperature vs. time for a typical sensing element and flowing material in response to the application of heat thereto.

It has been found that the use of a diode package alone substantially fully exposed to the flow of material may provide too rapid a thermal response characteristic compared to that of the flowing materials involved. Shown in FIG. 9 are two curves of thermal characteristics as a function of time in response to an abrupt increase (e.g., a "step" increase) in air temperature. Curve 51 represents the temperature response of a fully exposed temperature sensor, while curve 52 represents the thermal behavior of the material being processed. The material temperature is seen to lag behind that of the sensor temperature, as articulated earlier. However, the structure shown in FIG. 8 permits a sufficient amount of the diode package to be exposed to the flowing material, while the use of the stainless steel and epoxy mount therefore tends to produce a slower thermal response characteristic for the overall sensor assembly so that it more effectively approximates the thermal response characteristics of the various flowing materials which are expected to be used in the apparatus of the invention. Hence, the temperatures reported by the thermometric apparatus tend to reflect accurately those of the flowing material, and the disparities between curves 51 and 52 of FIG. 9 are effectively reduced.

In an alternative, and preferred, embodiment of the invention, a temporal thermal averaging algorithm is used to achieve the desired thermal characteristics by suitably processing the raw temperature data. In effect, such an algorithm filters the raw thermometric information so as to correct for mismatches in the dynamic thermal characteristics between the flowing material and the thermometric equipment, such filtering operation in the processor resulting in an accurately measured value for the temperature of the flowing material, as discussed earlier. Successful filtering is made practical by the fact that the actual material temperature lags that measured by the sensors. Hence, implementing an algorithm that adds a compensatory lag to the raw thermometric data is a relatively straightforward operation, using mathematical techniques that are well within the skill of those in the art.

Figure 7:
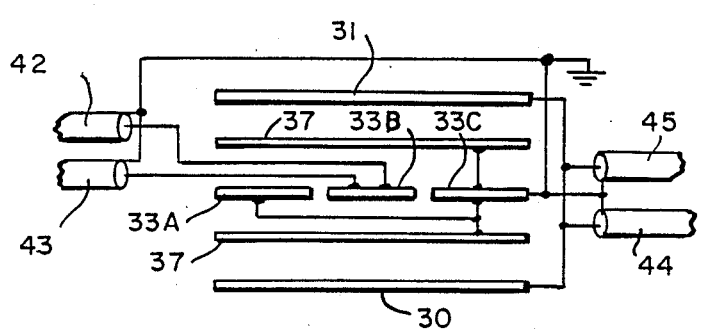
FIG. 7 shows the wiring diagram for the sensed output voltages from the sensing elements of FIGS. 4-6.

As can be seen in FIG. 7, the barrier shields 37 are connected to ground as well as to the shielded portions of the cables which are connected to the electrodes for measuring the voltage values between said electrodes. The upper and lower split elements 33A and 33C are grounded, while the center split element 33B is connected to the center conductors of cables 42 and 43. The outer electrode 30 and the inner electrode 31 are connected to the center conductors of cables 44 and 45. The cables carrying such sensor voltages at the elements 30, 31, and 33B are supplied to the sensor analog electronic circuitry as discussed above with reference to FIG. 2.

This particular sensing element depicted in FIGS. 4-7 effectively provides simultaneously voltages from each of the temperature sensing elements and the electrode elements thereof so as to permit accurate conversion of said sensed voltages to usable DC voltages which can then be converted to digital signals at A/D converter 21. The digital signals are then appropriately utilized to compute the spatially averaged and temporally compensated temperature of the flowing material, and to compute the required dielectric loss and capacitance values of the sensor using known computational techniques. Such values can then be used in Eqs.. (3) or (4) for permitting the moisture content of the material flowing through the sensor to be suitably monitored on a continuing basis.

As can be seen best in FIG. 1, the overall sensing element is made sufficiently large so that a substantial portion of the continually flowing material passes through the sensing element. Thus, the temperature, dielectric loss, and capacitance of a large sample thereof are continually measured and more effectively represent the measured characteristics of the material in comparison with prior art systems which normally make measurements of only relatively small samples of material at any given time. For example, while a prior art system may make measurements on a few grams of material, the system of the invention can continually make its measurement on many pounds of material, perhaps, at any given time.

There are two conflicting requirements that determine the practical range of sensor sizes. On the one hand, the flow-through region of the sensing element must possess a large enough cross-sectional area so that the flow of material is not impeded. In addition, a relatively large sensor size is desirable so that the amount of material present within the sensor is relatively large to reduce errors related to measuring the properties of a sample of limited size, as discussed above. However, if the spacing between sensor electrodes is increased to improve flow characteristics, the capacitance tends to decrease, degrading the sensitivity of the device. If this spacing is made too large, the sensitivity of the instrument can degrade to a point that determinations of moisture content cannot be made with the requisite accuracy. In general, it is found that a minimum empty-sensor capacitance of 10–20 pF is required to perform measurements to the desired accuracy. Hence, the practical range of sensor sizes is determined as a compromise between the requirements just discussed.

Moreover, while prior systems tend to use a single temperature probe in a particular sample, the technique of the invention uses a plurality of temperature probes at spaced locations, both radially and vertically (in elevation), so as to provide a better overall spatially averaged temperature measurement.

While it may be desirable in some applications to utilize a larger number of struts and temperature sensors than shown in FIGS. 4–7, it has been found that the use of three struts and four temperature sensors is acceptable for most applications and does not present an overly complex or expensive form for the sensing element desired.

As can be seen with reference to FIGS. 1 and 2, the sensed voltages are supplied by suitable cables to the computation circuits. The partitioning of sensing elements and computation circuitry permits high accuracy computations to be made without limiting the operational temperatures of the sensors involved since the electronic circuitry does not need to be contained within the sensing element. The signals can be carried a reasonable distance from the sensor (e.g., two meters) or can be mounted in relatively close proximity to the sensor depending on the application in which the system is used. The signal cabling from the sensors can be selected to be of a high-temperature, high-abrasion type since the materials being measured flow through the sensor and are in direct contact with the cables and at relatively high temperatures.

While the embodiments discussed above represent currently preferred embodiments of the invention, modifications thereof within the spirit and scope of the invention may be made by those in the art. Hence, the invention is not to be construed as limited thereto except as defined by the appended claims.

What is claimed is:

1. A method of determining the moisture content of a continually flowing material comprising the steps of
    causing said material to flow continually through a region defined by an operating sensor capacitance element;
    continually determining the spatially averaged temperature of said material as said material flows through said region using a plurality of temperature sensors, each of said temperature sensors being configured so that the thermal response characteristics thereof substantially approximate the thermal response characteristics of the flowing material;
    continually determining therefrom the loss and capacitance of said operating sensor capacitance element as said material flows through said region; and
    continually determining the moisture content M of said material in response to said spatially averaged temperature determination and said loss and capacitance determination regardless of changes in the packing density of said material as said material flows through said region in accordance with the following relationship:

$$M = \frac{Lm - (Ko + Kt*T)*C - (Bo + Bt*T)*Com/Cor}{(Km + Ktm*T)*C + (Bm + Btm*T)*Com/Cor}$$

where Lm is the dielectric loss, T is the spatially averaged temperature, C is the capacitance, Bo, Bt, Bm, Btm, Ko, Kt, Km and Ktm are predetermined coefficients, Cor is the pre-determined capacitance of a reference sensor capacitance element when no material is present in the region defined by said reference sensor capacitance element and Com is the capacitance of said operating sensor capacitance element when no material is present in the region defined by said operating sensor capacitance element.

2. A method in accordance with claim 1 and further wherein said region is made sufficiently large to permit the determination of the temperature of said flowing material at a plurality of points within said region so that the spatially averaged temperature of a relatively large sample of said flowing material can be determined at any one time.

3. A method in accordance with claim 1 and further wherein said region is made sufficiently large to avoid restriction of material flow.

4. A method in accordance with claim 1 and further wherein said region is made sufficiently small to permit the accurate determination of said loss and capacitance by providing a certain minimum capacitance.

5. A method in accordance with claim 4 wherein said minimum capacitance lies within a range of approximately 10–20 picofarads.

6. A method in accordance with claim 1 wherein the steps of continually determining the loss and capacitance and average temperature and thereby continually determining the moisture content are performed at a position which is remote from the material flowing through said sensor element.

7. An apparatus for determining the moisture content of a continually flowing material comprising
    a sensing capacitance means defining a region through which said material can continually flow and including a plurality of temperature sensing means for continually sensing the spatially averaged temperature of said material, wherein the dynamic thermal response of said temperature sensing means matches the dynamic thermal response of said material as said material continually flows through said region, said sensing capacitance means further including a plurality of concentrically mounted cylindrical members interconnected by a plurality of spaced radial struts, at least one of said temperature sensing means being positioned on each of said struts;
    means for continually determining the dielectric loss and capacitance of said sensing capacitance means as said material continually flows through said region; and
    means responsive to said spatially averaged temperature and to said dielectric loss and capacitance for continually determining the moisture content of said material regardless of changes in the packing density of said material as it flows through said region.

8. An apparatus in accordance with claim 7 wherein said plurality of temperature sensor elements are positioned at different radial points on said struts and at different elevation points within said region.

9. An apparatus in accordance with claim 7 wherein at least one of said cylindrical members comprises a plurality of separate cylinders mounted one above the other on said struts.

10. An apparatus in accordance with claim 7 and further wherein at least one of said struts has at least two temperature sensor elements mounted thereon at different elevations of said sensing means.

11. An apparatus in accordance with claim 7 wherein the thickness of said cylindrical members is substantially smaller than the distance between them so as to minimize resistance to the continual flow of said material through said sensing means.

12. An apparatus in accordance with claim 7 and further including shield members mounted on each side of and spaced from each temperature sensing means on each said strut.

13. An apparatus in accordance with claim 7 wherein said moisture content determining means comprises a microprocessor means.

14. An apparatus in accordance with claim 13 wherein said microprocessor means responds to said spatially averaged temperature, dielectric loss and capacitance for continually determining said moisture content in accordance with the following relationship:

$$M = \frac{Lm - (Ko + Kt*T)*C - (Bo + Bt*T)}{(Km + Ktm*T)*C + (Bm + Btm*T)}$$

where M is the moisture content, Lm is the dielectric loss, T is the spatially averaged temperature, C is the capacitance, and Bo, Bt, Bm, Btm, Ko, Kt, Km and Ktm are predetermined coefficients.

15. An apparatus in accordance with claim 13 wherein said microprocessor means responds to said spatially averaged temperature, dielectric loss and capacitance for determining said moisture content when using different sizes for said sensing capacitance means in accordance with the following relationship:

$$M = \frac{Lm - (Ko + Kt*T)*C - (Bo + Bt*T)*Com/Cor}{(Km + Ktm*T)*C + (Bm + Btm*T)*Com/Cor}$$

where M is the moisture content, Lm is the dielectric loss, T is the spatially averaged temperature, C is the capacitance, Bo, Bt, Bm, Btm, Ko, Kt, Km and Ktm are predetermined coefficients, Cor is the capacitance of a reference sensing capacitance means having a first size, Cor being the capacitance when no material is present in the region defined by said reference sensing capacitance means and Com is the capacitance of any other sensing capacitance means having a different size than that of said reference sensing capacitance means, Com being the capacitance when no material is present in the region defined by said other sensing capacitance means.

16. An apparatus in accordance with claim 12 wherein each of said temperature sensing means comprises
 a thermally sensitive element;
 a stainless steel collar member in which said element is mounted, the electrical leads from said element extending through said collar member, said leads being encapsulated with a high temperature epoxy material, at least a selected portion of said element being exposed to said continually flowing material, the amount of exposure of said selected portion being arranged so that the thermal response characteristics of said device substantially matches the thermal response characteristics of said continually flowing material, whereby the spatially averaged temperature of the flowing material is determined in accordance with the dynamic thermal response of the flowing material.

17. An apparatus in accordance with claim 13 wherein said microprocessor means further responds to said spatially averaged temperature measurement so as to determine a temporally compensated temperature which is compensated for the dynamic thermal response of said material.

* * * * *